United States Patent [19]

Smith

[11] 4,436,426
[45] Mar. 13, 1984

[54] HIGH-PRECISION REFLECTOMETER

[75] Inventor: Irl W. Smith, Newton, Mass.

[73] Assignee: Raytheon Company, Lexington, Mass.

[21] Appl. No.: 205,404

[22] Filed: Nov. 10, 1980

Related U.S. Application Data

[63] Continuation of Ser. No. 866,893, Jan. 3, 1978, abandoned.

[51] Int. Cl.³ .................... G01B 11/30; G01J 4/00; G01N 21/55
[52] U.S. Cl. .................................. 356/369; 356/371; 356/445
[58] Field of Search .............. 356/445, 446, 447, 448, 356/371, 369

[56] References Cited

U.S. PATENT DOCUMENTS

| | | | |
|---|---|---|---|
| 2,808,755 | 10/1957 | Millen | 356/448 |
| 3,277,773 | 10/1966 | White | 356/447 |
| 3,402,631 | 9/1968 | Potter | 356/369 |
| 3,914,057 | 10/1974 | Smith et al. | 356/369 |
| 3,972,619 | 8/1976 | Stevens | 356/369 |

Primary Examiner—John K. Corbin
Assistant Examiner—Rodney B. Bovernick
Attorney, Agent, or Firm—Richard M. Sharkansky; Herbert W. Arnold; Joseph D. Pannone

[57] ABSTRACT

A reflectometer for precisely measuring the reflectivities of mirrors by performing two sequential measurements each of which is related to a different function of the reflectivities of a reference mirror and the mirror under test. For the first measurement, the two mirrors are arranged so that a beam of light is reflected alternately from the reference mirror and from the test mirror to an output detector to produce an output signal related to the difference of the reflectivities. In the second measurement, the mirrors are positioned so that the beam passes to the output detector directly and, alternately, after reflection from first the reference mirror and then the test mirror, thereby producing an output signal related to the product of the reflectivities. The reflectivity of the test mirror is then calculated from the two output signal quantities.

16 Claims, 7 Drawing Figures

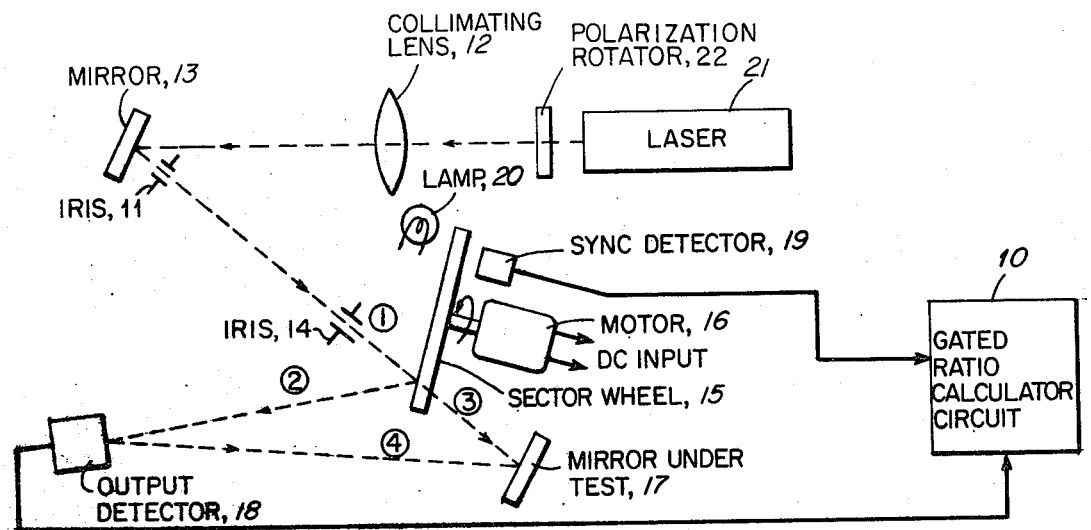
FIG. IA
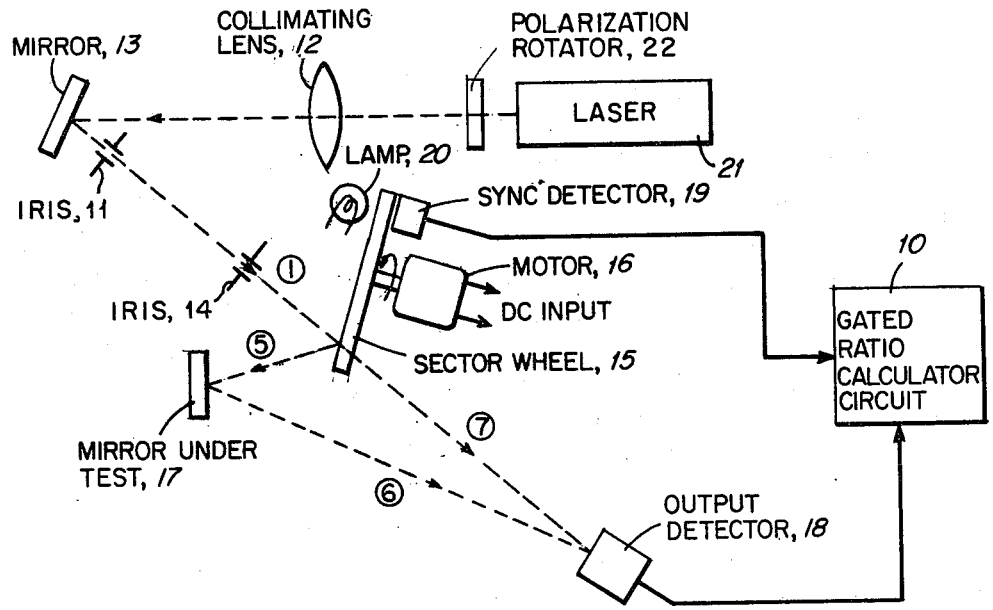
FIG. IB
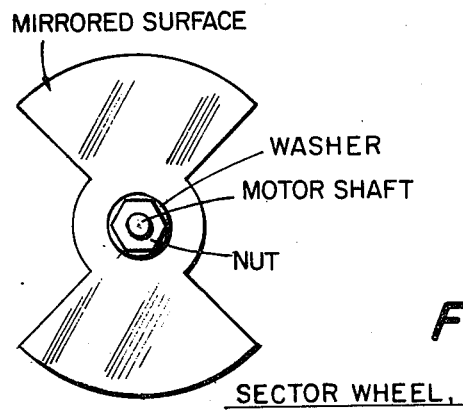
FIG. 2

HIGH-PRECISION REFLECTOMETER

CROSS REFERENCE TO RELATED CASES

This is a continuation of application Ser. No. 866,893, filed Jan. 3, 1978 now abandoned.

BACKGROUND OF THE INVENTION

1. Field of the Invention

The invention relates to the class of test devices known as reflectometers which are used for measuring the reflectivity of mirrors or other reflecting devices.

2. Description of the Prior Art

Developments in the fields of laser gyroscopes and high energy beam steering have required the production of mirrors having exceptionally high reflectivities. In parallel with the requirement for attaining high reflectivities, there exists the requirement to measure the reflectivity of such mirrors to extremely high precision. For many present day systems, mirror reflectivities R in excess of 0.99 are required. Unfortunately, most prior art reflectivity measuring techniques permitted the reflectivity to be measured to an accuracy of no greater than 1%. Hence, the error in the measurement of the loss L, defined as $1-R$, of such high reflectivity mirrors could be more than 100%.

In the past, the most common technique for measuring the reflectivity of the mirror was to determine the proportions of energy incident upon a mirror which were lost due to transmission, absorption, and scattering, the reflectivity then being computed by simply subtracting the sum of these from unity. Typically, the fraction S scattered would be 0.002, the fraction A absorbed 0.002, and the fraction T transmitted 0.0003. T may be determined most simply by measuring the incident and the transmitted intensities for given beam of light. This measurement can be done to an accuracy of approximately 1%. S, the fraction scattered, may be measured to a somewhat lesser accuracy by the use of an integrating sphere. A, the fraction absorbed, is the most difficult of the three quantities to be measured and can be determined to an accuracy of only about 10% with the use of calorimetry techniques if a sufficiently powerful light source is available. For the wavelengths typically used in laser gyroscopes and in the visible spectrum, a sufficiently powerful source is not generally available which would permit accurate determination of A. In summary, this technique is both cumbersome and inaccurate for the types of measurement for which the present invention is intended.

SUMMARY OF THE INVENTION

Accordingly, it is an object of the present invention to provide a reflectometer capable of measuring the losses of high reflectivity mirrors to a precision in excess of 1%.

Furthermore, it is an object of the present invention to provide such a reflectometer capable of performing the required measurements both quickly and easily.

These, as well as the other objects of the invention, may be met by providing the combination of first and second reflecting means with means for producing first and second signals each of which corresponds to a different mathematical function of the reflectivities of the reflecting means. To produce the two signals, a beam of electromagnetic radiation is directed toward the reflecting means. The position of at least one of the reflecting means with respect to the beam is varied in order to vary the path of the beam on its way to a detector. The detector produces signals which correspond to the intensity of the beam as it is reflected by one or both of the reflecting means or as it arrives directly.

The invention may also be practiced by providing the combination of first and second reflecting means and means for producing first and second signals with the first signal being a function of the sums of the reflectivities of the first and second reflecting means and the second being a function of the product of the reflectivities. The signal producing means may include means for cyclically varying the position of at least one of the reflecting means so that the reflecting means is alternately in and out of the path of the beam of electromagnetic energy. A detector is provided which produces an output signal in accordance with the intensity of an incident beam of electromagnetic energy. In a preferred embodiment, the first signal is produced by reflecting the beam from the first reflecting means to the detecting means, then removing the first reflecting means from the path of the beam and reflecting the beam from the second reflecting means to the detecting means. The second signal is then produced by reflecting the beam from the first reflecting means to the second reflecting means, then to the detecting means, and subsequently allowing the beam to reach the detecting means without being reflected by either of the reflecting means.

Objects of the invention may also be met by practicing the method comprising the steps of producing a beam of electromagnetic energy, reflecting the beam with first reflecting means to intensity determining means, reflecting the beam with second reflecting means to the intensity determining means, reflecting the beam with the first reflecting means to the second reflecting means and then to the intensity determining means, and directing the beam directly to the intensity determining means without reflection by either the reflecting means. It is to be noted that these steps, after the first, may be performed in any order. Further, there may be performed the steps of producing a first signal in proportion to the ratio of the output of the intensity determining means upon reflecting the beam with the first reflecting means to the intensity determining means to the output of the intensity determining means upon reflecting the beam with the second reflecting means to the intensity determining means, and producing a second signal in proportion to the ratio of the output of the intensity determining means upon reflecting the beam with the first reflecting means to the second reflecting means then to the intensity determining means without reflection by either the first or the second reflecting means. The reflectivities of either of the reflecting means may then be calculated from the first and second signals. Both of the first and second signals may be produced by alternately coupling the output of the intensity determining means to first and second low-pass filter means and producing a signal in proportion to the ratio between the outputs of the first and second low-pass filter means.

The invention may further be practiced by a reflectometer comprising the combination of means for producing a collimated beam of light, a sector wheel having a mirrored surface disposed in the path of the beam to alternately reflect and pass the beam as the sector wheel is rotated, a motor for rotating the sector wheel, means for positioning a mirror under test alternately at first and second locations with the first location being in the path of the beam as it is passed by the sector wheel and the second location being in the path of the beam as it is reflected from the sector wheel, and an output detector. The beam of light should be incident upon the detector wheel at an angle less than 90°. The output detector is positioned at a third location such that, when the mirror under test is positioned at the first location, the detector alternately receives the beam as it is reflected from the sector wheel and as it is reflected from the mirror under test. The output detector is to be positioned at a fourth location when the mirror under test is positioned at the second location, such that the detector will alternately receive the beam as it is reflected from both the sector wheel and the mirror under test and directly without reflection from either the sector wheel or the mirror under test. There may be coupled to the output detector means for producing a signal corresponding to the ratio between first and second states of the output signal from the detector. The first state corresponds to the amplitude of the output signal from the detector with the beam incident upon the sector wheel minus the output signal from the detector without the beam being incident upon the sector wheel, and with the second state corresponding to the amplitude of the output signal from the detector with the beam incident upon the sector wheel plus the output signal from the detector without the beam being incident upon the sector wheel. In a preferred embodiment, the signal producing means includes means for amplifying the output signal from the detector, means for inverting the amplified output signal such as with an amplifier having a gain of minus one, means for producing a signal representing the difference in amplitude between the first and second states of the output signal from the detector, a first low-pass filter coupled to the output of the signal producing means, means for producing a signal representing the sum of the amplitudes of the first and second states of the output signal from the detector, a second low-pass filter coupled to the output of the sum signal producing means, and means for producing a signal representing the ratio of the output of the first and second filters. There may further be provided means for converting the signal representing the ratio to digital form. Means may also be provided for producing a video indication of the value of the signal representing the ratio. The difference and sum signal producing means may each have one or more switching means therein. Means may also be provided for operating the switch means in synchronization with the movement of the sector wheel. The beam producing means is preferably a source of laser light.

BRIEF DESCRIPTION OF THE DRAWINGS

FIG. 1A is a diagram of a reflectometer in accordance with the present invention in a first configuration;

FIG. 1B shows the apparatus of FIG. 1A in a second configuration;

FIG. 2 shows a front view of the sector wheel of the apparatus shown in FIGS. 1A and 1B;

DESCRIPTION OF THE PREFERRED EMBODIMENTS

Figure 3:
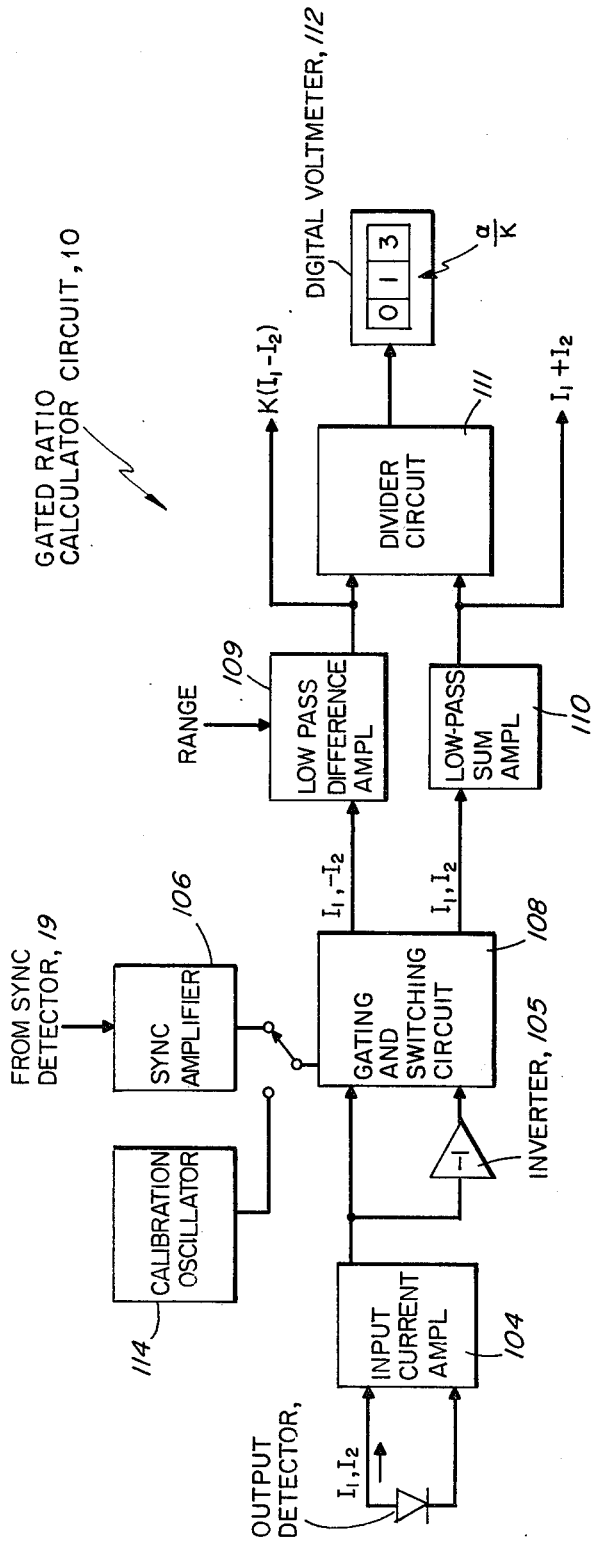
FIG. 3 is a block diagram of the gated ratio calculator circuit of the apparatus of FIGS. 1A and 1B.

Referring first to the view of FIG. 1A, there is shown a diagram of a reflectometer in a first configuration. A continuous beam of polarized light is produced by laser source 21. Polarization rotator 22 is a half-wave plate. Collimating lens 12 renders the beam substantially parallel. The beam is then reflected from mirror 13 to irises 11 and 14 where any light not traveling substantially parallel to the main body of the beam is clipped off. Other beam collimating schemes may be used depending upon the spot size and area of the mirror under test for which the reflectivity is to be measured.

After emerging from iris 14, the beam passes to sector wheel 15. Sector wheel 15 is shown in a front view of FIG. 2. The device is formed as a circular disc with two sectors removed as shown. The surface disposed toward iris 14 is mirrored. A washer and nut secure sector wheel 15 to the shaft of motor 16. Other arrangements may be used as well for the combination of sector wheel 15 and motor 16. For example, a rectangular mirror moved in a sideways back-and-forth motion will perform the desired function.

DC motor 16 rotates sector wheel 15 so that the incoming beam of laser light is alternately reflected along path 1–2 to output detector 18 and permitted to pass along path 1–3–4 being reflected from test mirror 17 to output detector 18. The rate of rotation of sector wheel 15 produced by motor 16 is preferably at a frequency asynchronous with the local power line of other periodic source which may cause interference.

An output current signal is produced by output detector 18 in proportion to the amplitude of the beams incident thereupon. When the beam passes along the path 1–2 being reflected by sector wheel 15, an output current $I_1$ is produced which is in proportion to the reflectivity of the mirrored surface of sector wheel 15. Similarly, when the beam passes along the path 1–3–4, reflected by test mirror 17, an output current $I_2$ is produced which is in proportion to the reflectivity of test mirror 17. The output signals from output detector 18 are coupled to gated ratio calculator circuit 10 which operates in a manner to be described below.

A synchronization signal needed for the operaton of gated ratio calculator circuit 10 is also produced by the apparatus of FIG. 1A. A lamp 20 is positioned as shown opposite sync detector 19 so that the path from lamp 30 to sync detector 19 falls at a 180° from the position at which the incoming laser light beam strikes sector wheel 15. As sector wheel 15 is rotated, the light produced by lamp 20 is alternately passed and interrupted, producing a substantially square wave synchronization signal at the output of sync detector 19. The circuitry of sync detector 19 and the circuitry interconnecting lamp 20, motor 16, and sync detector 19 are discussed below in conjunction with the description of FIG. 5.

Gated ratio calculator circuit 10, in the manner described below, computes a quantity $$a = K \frac{I_1 - I_2}{I_1 + I_2},$$

where K is a scale factor, from the two values of output current from detector 18 produced by rotation of sector wheel 15. Because $I_1$ is in proportion to the reflectivity of the mirror under test and $I_2$ is in proportion to the reflectivity of the reference mirror, the quantity $\alpha_a$ is produced for the configuration of FIG. 1A as $$\alpha_a = K_a \frac{R_r - R_t}{R_r + R_t}.$$

After the numeric value of $\alpha_a$ is determined using the configuration of FIG. 1A, the apparatus is reconfigured as shown in FIG. 1B. Test mirror 17 is positioned in the path of the beam as it is reflected from sector wheel 15 at substantially the same distance from the sector wheel 15 as it was in the configuration of FIG. 1A. Output detector 18 is moved to a position at the rear of sector wheel 15 so that the beam passing sector wheel 15 in the non-reflecting position strikes the surface of output detector 18 at the same spot as the beam reflected by test mirror 17.

With sector wheel 15 in the reflecting position as shown, the incident beam will be reflected along path 1-5-6 being reflected by both sector wheel 15 and test mirror 17 to output detector 18. In this case, the output current $I_1$ from output detector 18 will be in proportion to the product of the reflectivities of the mirrored surface of sector wheel 15 and test mirror 17. With sector wheel 15 in the non-reflecting position, the beam will pass along path 1-7 directly to output detector 18, threby producing an output current $I_2$ in proportion only to the amplitude of the beam. For this case, gated ratio calculator circuit 10 computes a quantity $$\alpha_b = K_b \frac{R_r R_t - 1}{R_r R_t + 1}.$$

From the measured numerical values of $\alpha_a$ and $\alpha_b$ and their known relationships to the reflectivities of both the reference and test mirrors, the reflectivities of each may be computed. Solving the two equations immediately above simultaneously, $$R_t = \left[ \frac{(1 + \alpha_b/K_b)(1 - \alpha_a/K_a)}{(1 + \alpha_a/K_a)(1 - \alpha_b/K_b)} \right]^{\frac{1}{2}}.$$

This equation may be approximated by $R_t = 1 + (\alpha_b/K_b - \alpha_a/K_a)$. Similarly, $$R_r = \left[ \frac{(1 + \alpha_a/K_a)(1 + \alpha_b/K_b)}{(1 - \alpha_a/K_a)(1 - \alpha_b/K_b)} \right]$$

which may be approximated by $R_r = 1 + (\alpha_a/K_a + \alpha_b/K_b)$.

Although it is not necessary to compute the reflectivity of the reference mirror, it is useful to do so with the measurement of each test mirror to ensure that the apparatus is functioning properly. The value of $R_r$ should be substantially constant from measurement to measurement.

Referring next to FIG. 3, there is shown a block diagram of gated ratio calculator circuit 10 as used with the apparatus of FIGS. 1A and 1B. The output signals from output detector 18 are amplified by input current amplifier 104 to a sufficient level for use by the remainder of the circuitry. The amplified output from input current amplifier 104 is inverted by inverter 105 so that amplified signals in proportion to $I_1$, $I_2$, $-I_1$, and $-I_2$ are available.

Gating and switching circuit 108 performs two major functions. First, this circuit gates through to the remainder of the circuitry only the central portion of each of the $I_1$ and $I_2$ signals. This is advantageous because noise may be present on the signals near the transitions between the $I_1$ and $I_2$ current levels produced as the edge of the sector wheel passes through the beam. Secondly, gating and switching circuit 108 alternately couples the $I_1$ and $-I_2$ signals to low-pass difference amplifier 109 and the $I_1$ and $I_2$ signals to low-pass sum amplifier 110. The operation of gating and switching circuit 108 is synchronized by the amplified pulses produced by sync detector 19. Amplification of these pulses is done with sync amplifier 106.

Low-pass difference amplifier 109 is a two-stage amplifying and integrating filter with a switchable gain set by a range control. The multiplicative factor $K (K = K_a, K_b)$ in the quantity $K(I_1 - I_2)$ is supplied by a low-pass difference amplifier 109. The range control is necessary because the difference between $I_1$ and $I_2$ may be very small, such as in the case when the reflectivities of the test mirror and the mirrored surface of the sector wheel are nearly identical. Additional amplification may then be necessary to bring the signal representing $\alpha$ to an acceptable level. Low-pass sum amplifier 110 is also an amplifying integrating filter but has lower gain as the level of the signal $I_1 + I_2$ is much greater than that of $I_1 - I_2$.

The ratio $$\alpha = K \frac{I_1 - I_2}{I_1 + I_2}$$

is next computed by divider circuit 111. Divider circuit 111 in the preferred embodiment is an analog signal divider circuit producing an analog voltage on its output in proportion to the ratio between the two input signals. Digital voltmeter 112, coupled to the output of the divider circuit 111, produces a visual digital indication of the value of the output signal from divider circuit 111 which is directly read as $\alpha$. In an alternate embodiment, the outputs of low-pass difference amplifier 109 and low-pass sum amplifier 110 are converted directly to digital form and the ratio calculated using a digital calculation circuit.

Figure 4:
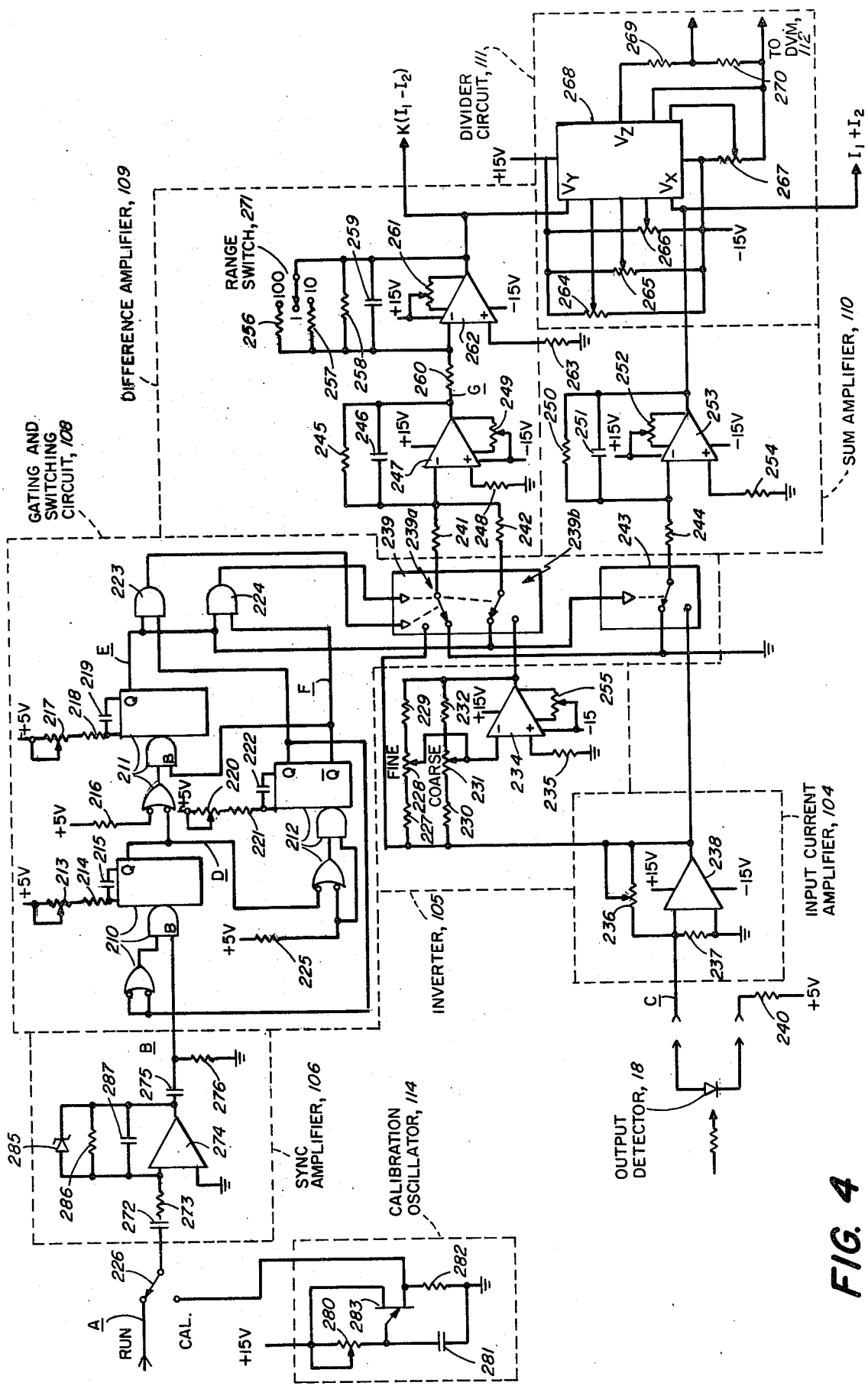
FIG. 4 is a detailed schematic diagram of the circuitry shown in block diagram form in FIG. 3.

Referring next to FIG. 4, there is shown a schematic diagram of the circuit shown in FIG. 3. Output detector 18, a silicon photodiode biased by +5 volts through resistor 240, is coupled to the inverting input of input current amplifier 104. The waveform of the signal produced by output detector 18 is shown as waveform C in FIG. 6. The level of waveform C switches between $I_1$ and $I_2$ current levels but with spikes and noise at the transition times. The gain of input current amplifier 104 may be set to a convenient level by adjusting potentiometer 236.

The output of input current amplifier 104 is coupled directly to gating and switching circuit 108 and also to the input of inverter 105. Inverter 105 is constructed with an operational amplifier with negative unity gain. The gain is precisely adjustable by fine and coarse gain adjustment potentiomenters 228 and 231. The offset of operational amplifier 234 is adjusted with potentiometer 255.

During test measurement operations, switch 226 is set to the RUN position to receive the square wave synchronization signal from sync detector 19. This signal is shown as waveform A in FIG. 6 below. The square wave signal is differentiated by the network including capacitor 272, resistor 273, and the feedback elements around amplifier 274 to produce a signal having pulses at the positive edge transitions of the square wave synchronizing signal. Zener diode 285 clamps the level of the output of operational amplifier 274 to a preferred level of 5.1 volts. Capacitor 275 and resistor 276 provide further filtering of the amplified signal removing high frequency spike components. The resulting pulsed synchronizing signal is shown as waveform B in FIG. 6.

Figure 6:
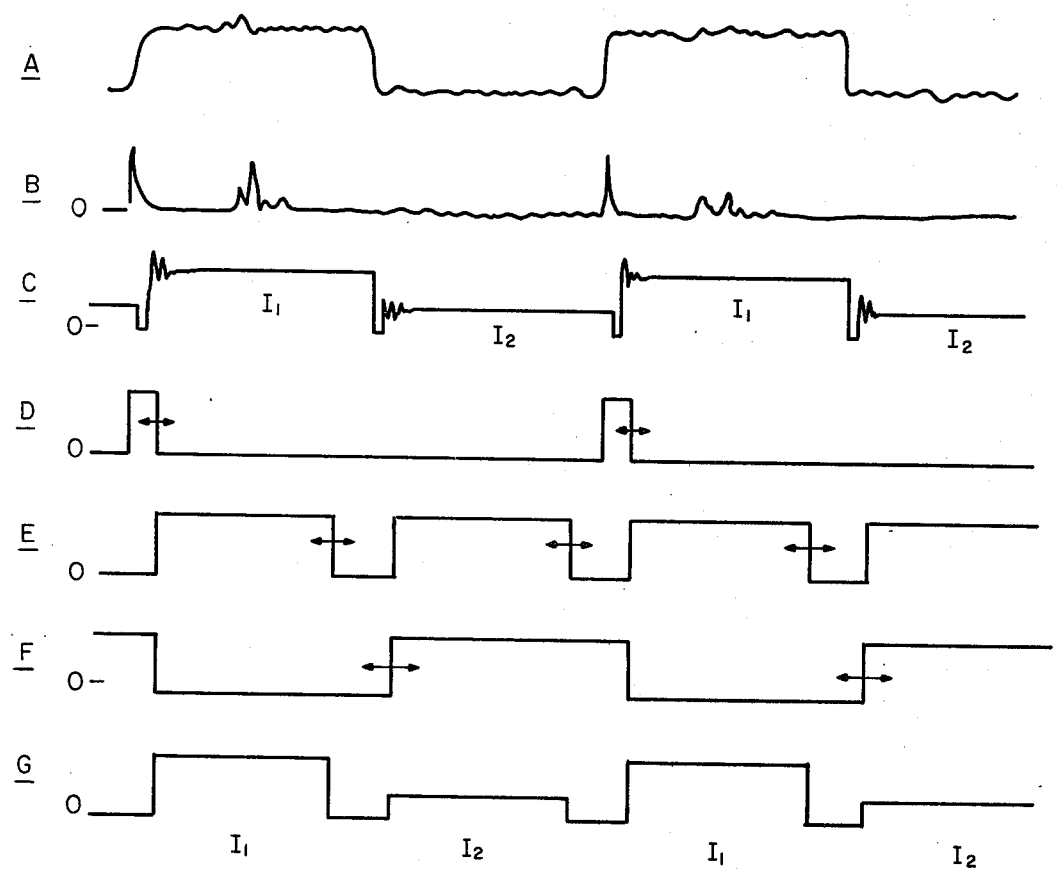
FIG. 6 shows a series of waveforms useful in understanding the operation of the preferred embodiment of the present invention.

The pulsed synchronizing signal is coupled to the Schmitt trigger input of monostable multivibrator 210. The pulsed signal shown as waveform D in FIG. 6 is produced thereby. The width of the pulse on the output of multivibrator 210 is adjusted by potentiometer 213. This width determines the time delay from the beginning of the input $I_1$ signal until the $I_1$ signal is coupled to the difference and sum amplifiers.

The output of multivibrator 210 is coupled to the inverting input of multivibrators 211 and 212, and the inverting output of multivibrator 212 is coupled to the non-inverting Schmitt trigger input of multivibrator 211. Also, the non-inverting output of multivibrator 212 is coupled to the inverting input of multivibrator 210 to provide a sync lock-out feature so that extraneous pulses in the synchronizing signal do not erroneously trigger the circuitry. The resulting output waveforms from multivibrators 211 and 212 are shown as waveforms E and F in FIG. 6. These outputs are coupled to the inputs of AND gates 223 and 224 to provide the control signals for FET swtich 239. The non-inverting output of multivibrator 211 forms the control signal input to FET switch 243. The switch-off time for both $I_1$ and $I_2$ signals may be adjusted by potentiometer 217 which determines the pulse width output from multivibrator 211. The switch-on time for $I_2$ may be adjusted by potentiometer 220 associated with multivibrator 212.

The inverting input of amplifier 247 is coupled through switch section 239a to the non-inverted incoming signal during the times when the $I_1$ signal is presented. Switch 239b couples the same input to the inverted signal when the $I_2$ signal is present. Both switch sections 239a and 239b are switched to the grounded position, as shown, during the transition period between the $I_1$ and $I_2$ signals to reduce the amount of noise and hence error in the output signal. The input of sum amplifier 110 is coupled through switch 243 to the non-inverted signal during the signal presentation times; during the signal transition times switch 243 couples the input of amplifier 253 to ground.

The output of amplifier 247 is coupled through resistor 260 to the inverting of input amplifier 262. The gain of this stage of amplification, and hence the value of the scale factor K, is determined by the value of feedback resistance chosen with range switch 271. With range switch 271 in the "1" position as shown, the gain of difference amplifier 109 will be such that the displayed value of $\alpha$ may be read directly. With range switch 271 in "10" position, the displayed value of $\alpha$ should be divided by 10 to determine the actual value. Similarly, with range switch 271 in the "100" position, the value of $\alpha$ read out should be divided by 100.

The output of difference amplifier 109 is coupled to the numerator input $V_z$ of divider integrated circuit 268 while the output of sum amplifier 110 is coupled as the denominator input $V_x$. The output signal representing the dividend is coupled out across the voltage divider formed by resistors 269 and 270. Digital voltmeter 112 is connected across resistor 270 to read the computed values of $\alpha$.

The apparatus shown in FIG. 4 should be calibrated before use. First, the output offset voltages of operational amplifiers 247, 253, and 262 should be set to zero using potentiometers 249, 252, and 261. Then the offset voltage of amplifier 234 should be set to zero by blocking the light input to output detector 18 and adjusting potentiometer 255 for zero output voltage ($I_1-I_2=0$).

Next, switch 226 is set to the CALIBRATE position. In this position, pulses produced by unijunction transistor calibration oscillator 114 similate the normally produced synchronization pulses from sync detector 19. Power is removed from motor 16 to halt the rotation of sector wheel 15. With sector wheel 15 stationary, the light input to output detector 18, and hence input current to input current amplifier 104, is constant. Hence, it will appear that $I_1$ equals $I_2$. Fine and coarse adjustment potentiometers 228 and 231, respectively, of inverter 105 are then adjusted to provide a zero output upon the output of difference amplifier 109 ($I_1-I_2=0$ again).

Offset and gain potentiometers 264-267 associated with divider integrated circuit 268 should be adjusted in accordance with the manufacturer's specifications.

Figure 5:
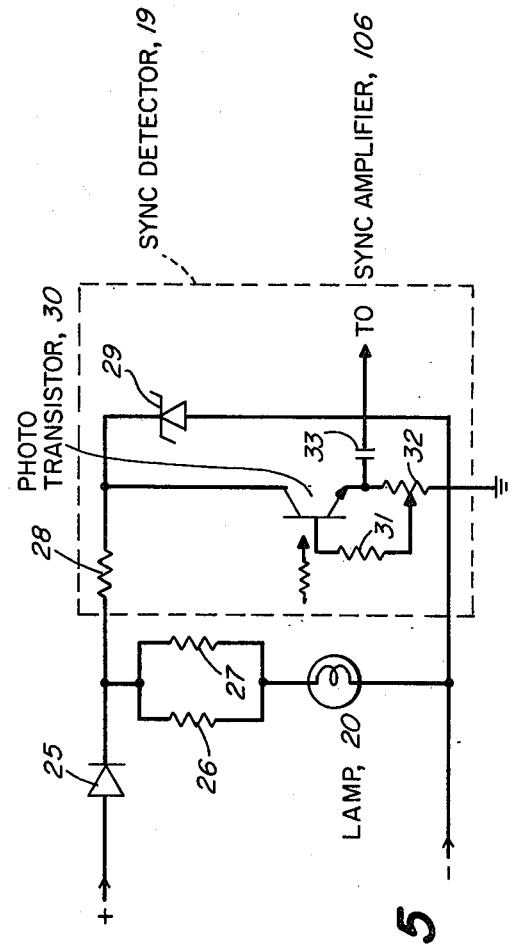
FIG. 5 is a schematic diagram of the sync detector circuit of the apparatus shown in FIGS. 1A and 1B.

Referring next to FIG. 5, there is shown the schematic diagram of sync detector 19 and associated circuitry. The same DC input which is applied to motor 16 is coupled through diode 25 to both sync detector circuit 19 and lamp 20 through current limiting resistors 26 and 27. Diode 25 prevents negative voltage transients from damaging the circuitry of sync detector 19. The DC voltage is coupled through collector resistor 28 to photo-transistor 30. The base of photo-transistor 30 is biased through resistor 31 coupled to the center tap of potentiometer 32 which is connected between emitter and ground. When sector wheel 15 permits the light output from lamp 20 to reach photo-transistor 30, current will flow through potentiometer 32 producing a pulsed output through output capacitor 33. Zener diode 29 clamps the maximum output voltage to a preferred level.

A listing of the parts types and various component values for the circuits shown in FIGS. 4 and 5 follows below in the Appendix.

This concludes the description of the preferred embodiments of the invention. Although preferred embodiments have been described, it is believed that numerous modifications and alterations thereto would be apparent to one having ordinary skill in the art without departing from the spirit and scope of the invention.

APPENDIX

| PARTS LIST FOR CIRCUITS OF FIGS. 4 AND 5 | |
|---|---|
| Ref. No. | Value |
| Capacitors | |
| 33 | 2.2 μf |
| 215 | 0.1 |
| 219, 281 | 0.2 |
| 222 | 0.68 |
| 251 | 0.47 |
| 246, 259 | 4 |
| 272, 275 | 0.02 |
| 287 | 33 pf. |
| Resistors | |
| 20 | 100 |
| 26 | 39, 2W. |
| 27 | 150 |
| 31 | 10 M. |
| 32, 228 | 1K, variable |

APPENDIX-continued

PARTS LIST FOR CIRCUITS OF FIGS. 4 AND 5

| Ref. No. | Value |
| --- | --- |
| 213, 217 | 25K, variable |
| 214, 218 | 2K |
| 216, 225 | 2.2K |
| 220 | 5K, variable |
| 221 | 5K |
| 227, 229, 244, 254 | 100K |
| 230, 232, 235, 241, 242, 248 | 11K |
| 231 | 200, variable |
| 236, 249, 255, 261 | 10K, variable |
| 237, 276 | 1K |
| 240 | 50 |
| 245 | 110K |
| 250 | 1 M. |
| 252, 269 | 10K |
| 257 | 450K |
| 258 | 4 M. |
| 260, 263 | 20K |
| 264, 265, 266, 280 | 50K, variable |
| 267 | 20K, variable |
| 273 | 33K |
| 282 | 510 |
| Diodes | |
| 25 | 1N4005 |
| 29, 285 | 5.1 volt Zener |
| 18 | UV-44B (EG&G Co.) |
| Transistors | |
| 30 | |
| 283 | 2N4870 |
| Integrated Circuits | |
| 210, 211, | Texas Instruments SN74121 |
| 223, 224 | Texas Instruments SN 7408 |
| 234, 247 | Analog Devices 506 |
| 238, 274 | Motorola 1458 |
| 239, 240 | Analog Devices 7512 |
| 253, 262 | Analog Devices 536 |
| 268 | Analog Devices 436 |

What is claimed:

1. A reflectometer for determining the reflectivity of reflecting means comprising:
   means for producing a beam of light;
   first and second reflecting means;
   means for producing a first signal which is a function of the difference of the reflectivities of said first and second reflecting means;
   means for producing a second signal which is a function of the product of said reflectivities; and
   means for producing an output signal as a function of said first and second signals, said output signal being a function of the reflectivity of at least one of said first and second reflecting means.

2. The reflectometer of claim 1 wherein:
   said first and second signal producing means comprise means for cyclically varying the position of at least one of said reflecting means.

3. The reflectometer of claim 2 wherein:
   said means for producing said beam comprises a laser.

4. The reflectometer of claim 2 wherein:
   said first and second signal producing means further comprise beam intensity detecting mean for producing said first or second signal in accordance beam, respectively.

5. The reflectometer of claim 3 wherein:
   said first signal is produced by reflecting said beam alternately from said first reflecting means to said detecting means and from said second reflecting means to said detecting means; and
   said second signal is produced by alternately reflecting said beam from said first reflecting means to said second reflecting means to said detecting means and allowing said beam to reach said detecting means witout being reflected by either of said reflecting means.

6. The method of determining reflectivity comprising the steps of:
   producing a beam of electromagnetic energy and producing a first measurement of the intensity of said beam;
   reflecting said beam with first reflecting means to intensity detecting means and producing a second measurement of the intensity of said reflected beam;
   reflecting said beam with second reflecting means to said intensity detecting means and producing a third measurement of the intensity of said reflected beam;
   reflecting said beam with said first reflecting means to said second reflecting means to said intensity means and producing a fourth measurement of the intensity of said reflected beam; and
   determining the reflectivity of at least one of said first and second reflecting means as a function of said intensity measurements.

7. The method of claim 6 wherein:
   said step of determining reflectivity comprises producing a first signal in proportion to the ratio of the difference of said second and third intensity measurements to the sum of said second and third intensity measurements; and
   producing a second signal in proportion to the ratio of the difference of said fourth and first intensity measurements to the sum of said fourth and first intensity measurement.

8. The method of claim 7 wherein:
   said step of determining reflectivity comprises deriving the reflectivity of at least one of said reflecting means from said first and second signals.

9. The method of claim 7 wherein:
   said steps of producing said first signal and/or said steps of producing said second signal comprises the step of:
   coupling alternately, additively and subtractively the output of said intensity detecting means to a first low-pass filter means;
   coupling said output additively to a second low-pass filter means; and
   producing a signal in proportion to the ratio between the outputs of said first and second filter means.

10. A reflectometer comprising in combination:
    means for producing a collimated beam of light;
    a sector wheel, said sector wheel having a mirrored surface disposed in the path of said beam to alternatively reflect and pass said beam as said sector wheel is rotated;
    a motor for rotating said sector wheel;
    means for positioning a mirror under test alternately at first and second locations, said first location being in the path of said beam as it is passed by said sector wheel and said second location being in the path of said beam as it is reflected from said sector wheel;
    an output detector; and
    means coupled to said output detector for producing a signal corresponding to the ratio between first and second functions of the output signal from said detector, said first function corresponding to the amplitude of the output signal from said detector with said beam incident upon said sector wheel minus the output signal from said detector without said beam being incident upon said sector wheel and said second function corresponding to the amplitude of the output signal from said detector with said beam incident upon said sector wheel plus the output signal from said detector without said beam being incident upon said sector wheel.

11. The combination of claim 10 wherein:
said signal producing means operates in synchronization with the movement of said sector wheel.

12. The combination of claim 11 wherein said signal producing means comprises:
means for amplifying the output signal from said detector;
means for inverting the amplified output signal;
means for producing a signal representing the difference in amplitudes between first and second states of said output signal from said detector;
first low-pass filter means coupled to the output of said difference signal producing means;
means for producing a signal representing the sum in amplitudes of said first and second states of said output signal from said detector;
second low-pass filter means coupled to the output of said sum signal producing means; and
means for producing a signal representing the ratio of the outputs of said first and second filter means.

13. The combination of claim 12 further comprising:
means for converting said signal representing said ratio to digital form.

14. The combination of claim 13 wherein said difference and sum signal producing means each comprise:
switch means.

15. The combination of claim 14 further comprising:
means for operating said switch means in synchronization with the movement of said sector wheel.

16. The combination of claim 10 wherein said beam producing means comprises:
a source of laser light.

* * * * *